United States Patent
Tsai et al.

(10) Patent No.: US 8,455,017 B2
(45) Date of Patent: Jun. 4, 2013

(54) ACTIVE SUBSTANCE FOR IMPROVING HYPERLIPIDEMIA AND HYPERCHOLESTEROLEMIA

(75) Inventors: Pi-Jen Tsai, Pingtung (TW); Hso-Chi Chaung, Pingtung (TW)

(73) Assignee: National Pingtung University of Science & Technology, Neipu Hsiang, Pingtung County (TW)

( * ) Notice: Subject to any disclaimer, the term of this patent is extended or adjusted under 35 U.S.C. 154(b) by 130 days.

(21) Appl. No.: 13/087,853

(22) Filed: Apr. 15, 2011

(65) Prior Publication Data

US 2012/0171315 A1 Jul. 5, 2012

(30) Foreign Application Priority Data

Dec. 29, 2010 (TW) ................. 99146604 A

(51) Int. Cl.
*A61K 36/21* (2006.01)
*A61P 3/06* (2006.01)
*A61P 9/00* (2006.01)

(52) U.S. Cl.
USPC .......................................... 424/725; 514/7.4

(58) Field of Classification Search
None
See application file for complete search history.

(56) References Cited

U.S. PATENT DOCUMENTS

| | | | |
|---|---|---|---|
| 4,684,628 | A | 8/1987 | Liu |
| 4,906,470 | A | 3/1990 | Liu |
| 5,487,894 | A | 1/1996 | Kovacs |
| 6,630,178 | B1 | 10/2003 | Høie |

FOREIGN PATENT DOCUMENTS

TW    I318882    1/2010

OTHER PUBLICATIONS

Tsai, P-J et al. J. Agric. Food Chem. (2010; Published on web Dec. 23, 2009). 58(2): 1020-1025. Thermal and pH stability of betacyanin pigment of djulis (*Chenopodium formosanum*) in Taiwan and their relation to antioxidant activity.*
Chio, E-H et al. Journal of Asia-Pacific Entomology. (2008) 11: 225-227. A bioassay for natural insect repellents.*
Tsai et al., "Effect of Nanogrinding on the Pigment and Bioactivity of Djulis (*Chenopodium formosanum* Koidz.)," Journal of Agricultural and Food Chemistry, 59, Feb. 9, 2011, pp. 1814-1820.

* cited by examiner

*Primary Examiner* — Michele Flood
(74) *Attorney, Agent, or Firm* — Muncy, Geissler, Olds & Lowe, PLLC

(57) ABSTRACT

An active substance of medication or health product for hyperlipidemia and hypercholesterolemia comprises djulis, and which can effectively inhibit the absorption of cholesterol, advance the metabolism of cholesterol, promote the anti-oxidation and decrease the accumulation of oxidized low-density lipoprotein-cholesterol in vessel walls of organisms.

4 Claims, 5 Drawing Sheets

ACTIVE SUBSTANCE FOR IMPROVING HYPERLIPIDEMIA AND HYPERCHOLESTEROLEMIA

BACKGROUND OF THE INVENTION

1. Field of the Invention

The present invention relates to an active substance for improving hyperlipidemia and hypercholesterolemia particularly to an active substance of medication or health product for hyperlipidemia and hypercholesterolemia.

2. Description of the Related Art

Hypercholesterolemia, hyperlipidemia and cardio-cerebrovascular disease are common issues to modern people, due to unbalance diet, malnutrition, and lack of proper exercises leading to accumulation of over fat in bodies. Generally, lifestyle changes, such as low-fat diet and physical activity, and appropriate medications are recommended to reduce high level of cholesterol in blood and finally to prevent from the said hypercholesterolemia, hyperlipidemia and cardio-cerebrovascular diseases. Conventional medications for hypercholesterolemia or hyperlipidemia include clofibrate or lactic acid bacteria, wherein the clofibrate can promote the activity of lipoprotein lipase and advance the degradation of cholesterol. Yet, the lactic acid bacteria have bile salt hydrolase, which can co-precipitate with bile salt and eliminate the bile salt with excretion so as to decrease the absorption of cholesterol in organisms. However, the conventional medications might leads to serious side effects, for example, gallstone, tumor, and damages to liver. As a result, there has a new approach of therapy for hypercholesterolemia and hyperlipidemia provided, by using natural substance and natural food to reduce the incidence of cardio-cerebrovascular diseases.

According to recent researches, the antioxidant system of organisms plays an important role in the prophylaxis of cardio-cerebrovascular diseases. It is reported that excess active oxygen in bodies will result in oxidized lipoprotein accumulated in vessel walls and finally become atheromatous plaques of vessel walls. The atheromatous plaques of vessel walls will aggravate the accumulation of oxidized low-density lipoprotein-cholesterol and increase the incidence to hyper-cholesterol or hyper-lipoprotein related diseases.

Accordingly, plenty of health product or natural substances are provided for reducing active oxygen in organisms and preventing from accumulation of oxidized cholesterol. A conventional natural substance, disclosed in Taiwan Patent No: I318882 and entitled "A USE OF *HIBISCUS SABDARIFFA* CALYX EXTRACT IN REDUCING LOW DENSITY LIPOPROTEIN, REDUCING TRIGLYCERIDE IN PLASMA OR INHIBITING ATHEROSCLEROSIS" provides an extract from *Hibiscus sabdariffa* to inhibit the oxidation of low-density lipoprotein-cholesterol and to decrease the risk of having cardio-cerebrovascular diseases.

However, the extract from *Hibiscus sabdariffa* only can provides general antioxidant ability and avoids the accumulation of cholesterol, instead of directly diminishing the absorption of cholesterol, and therefore, the efficiency of improving hyperlipidemia and hypercholesterolemia is low.

Furthermore, oats, also known as *Avena sativa* is another conventional natural substance for improving hyperlipidemia and hypercholesterolemia. Oats can promote the gastrointestinal function to eliminate cholesterol with excretions. In this way, the high level of cholesterol in blood of organisms will be improved so as to inhibit the invasion of cardio-cerebrovascular diseases. Nevertheless, the efficiency of lowering the oxidation of LDL by the antioxidants contained in oats is still not clear.

Hence, there is a pressing need of providing a new strategy of reducing the incidence to hyper-cholesterol or hyper-lipoprotein related diseases, for the sake of significantly inhibiting the absorption of cholesterol, advancing the antioxidant activity of organisms, avoiding the accumulation of oxidized low-density lipoprotein-cholesterol in vessel walls and finally preventing from cardiovascular-cerebrovascular disease.

SUMMARY OF THE INVENTION

The primary objective of this invention is to provide an active substance for improving hyperlipidemia and hypercholesterolemia, which contains djulis so as to be dramatically effective in blocking the absorption of cholesterol, advancing the metabolism of cholesterol, promoting the anti-oxidation of organisms and decreasing the accumulation of oxidized low-density lipoprotein-cholesterol (oxLDL-C) in vessel walls.

An active substance of medication for hyperlipidemia and hypercholesterolemia comprises djulis.

An active substance of health product for hyperlipidemia and hypercholesterolemia comprises djulis.

Further scope of the applicability of the present invention will become apparent from the detailed description given hereinafter. However, it should be understood that the detailed description and specific examples, while indicating preferable embodiments of the invention, are given by way of illustration only, since various more will become apparent to those skilled in the art from this detailed description.

BRIEF DESCRIPTION OF THE DRAWINGS

The present invention will become more fully understood from the detailed description given herein below and the accompanying drawings which are given by way of illustration only, and thus are not limitative of the present invention, and wherein.

Figure 1:
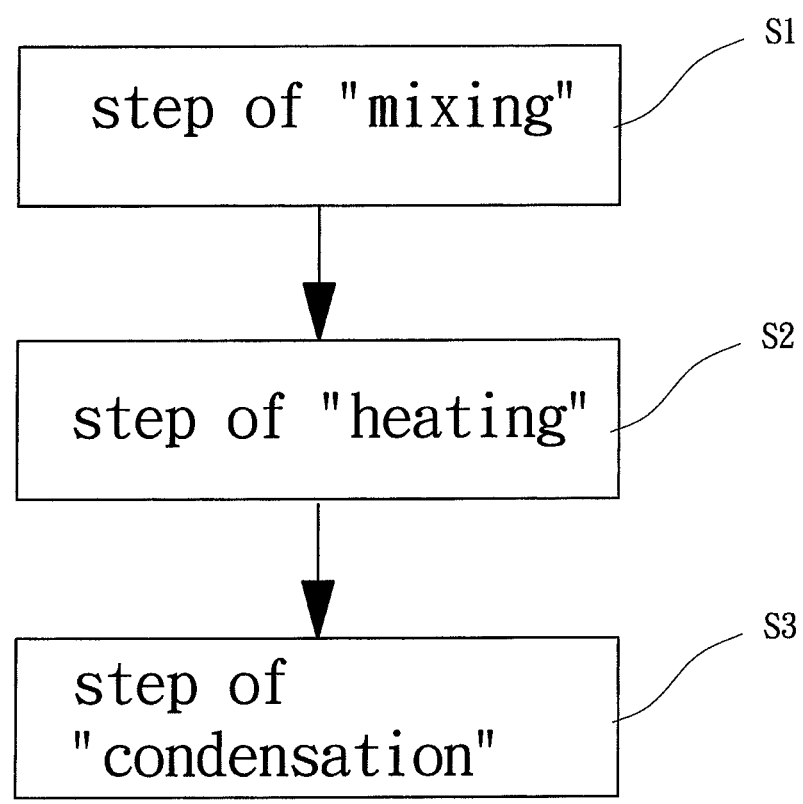
FIG. 1 is a flow chart illustrating a manufacturing method of djulis.

All figures are drawn for ease of explaining the basic teachings of the present invention only; the extensions of the figures with respect to number, position, relationship, and dimensions of the parts to form the preferred embodiment will be explained or will be within the skill of the art after the following teachings of the present invention have been read and understood. Further, the exact dimensions and dimensional proportions conforming to specific force, weight, strength, and similar requirements will likewise be within the skill of the art after the following teachings of the present invention have been read and understood.

DETAILED DESCRIPTION OF THE INVENTION

The present invention relates to an active substance for improving hyperlipidemia and hypercholesterolemia, which comprises djulis and is sufficient to inhibit the absorption of cholesterol, to advance the metabolism of cholesterol, to increase the anti-oxidation of organisms, also to prevent from accumulation of oxidized low-density lipoprotein-cholesterol (oxLDL-C) in vessel walls.

The dulis, also known as *Chenopodium formosanum* Koidz. is a traditional cereal in Taiwan but is less popular to local people due to its bitter taste. Generally, the dulis has plenty of nutrition, including starch, protein, dietary fiber and fatty acid, and is rich in antioxidants, such as polyphenols, γ-aminobutyric acid (GABA), bioflavonoids, superoxide dismutase (SOD) and betalains. Specifically, the djulis has a great amount of dietary fiber, with around 17.7% in total weight and being three times more than that of oats (5.1% only). With such amount of the dietary fiber, the djulis of the present invention can effectively remove cholesterol in digestive tracts and vessels, inhibit the absorption of cholesterol and advance the gastrointestinal function to eliminate cholesterol with excretions. Moreover, the polyphenols of the djulis can activate the antioxidant enzyme in organisms, and also inhibit the absorption of cholesterol whatever in cells or in digestive tracts. Next, the betalains of the djulis can inhibit the oxidation of the low-density lipoprotein-cholesterol (LDL-C), so that the accumulations of the oxidized low-density lipoprotein-cholesterol (oxLDL-C) in vessel walls, as well as cardiovascular and cerebrovascular diseases are avoided. Finally, the SOD of the djulis, acting as a powerful antioxidant enzyme, can scavenge free radicals and remove reactive oxygen species, such as $\cdot O_2^-$ and $\cdot OH$, from cells of organisms. The SOD of the djulis will transfer the free radicals to $O_2$ or $H_2O_2$ via a dismutation, and which can relieve the accumulation of the free radicals to cause any related diseases in organisms.

With such benefits from dietary fiber, polyphenols, betalains and SOD of the djulis, it is believed that the djulis of the present invention can be an active substance in health product or medication for hyperlipidemia and hypercholesterolemia. The djulis can efficiently advance the antioxidant activity of organisms, inhibit the absorption of cholesterol and increase the metabolism of cholesterol in organisms, reduce the accumulation of the oxLDL in vessel walls, and finally to prevent from any hyperlipidemia- and hypercholesterolemia-related diseases in organisms.

With reference to FIG. 1, the djulis of the present invention is processed under a step of "mixing S1," a step of "heating S2," and a step of "condensation S3" sequentially, to obtain a djulis paste. The djulis paste can be provided to any organisms with hypercholesterolemia or hyperlipidemia, in order to promote their antioxidant activity but reduce their high level of cholesterol in blood.

In the step of "mixing S1," a sample of djulis is prepared and ground into djulis powder. The djulis powder is mixed with a buffer to obtain a mixture. In the present embodiment, the djulis powder is preferably in the form of a microparticle, for example 1 to 20 µm. The buffer of the present embodiment is distilled water. Furthermore, the djulis powder of the present embodiment takes around 1 to 30% of total weight of the mixture so as to be easy to use in a following animal trial of the present invention.

In the step of "heating S2," the mixture is heated at 65 to 85° C. for 0.5 to 1 hour. With such arrangement, the starch of the djulis will transfer from β-starch to α-starch, which makes the starch of the djulis biodegradable. In the present embodiment, the preferable temperature of the heating is 70° C., and the preferable time of the heating is 0.5 hour, in order to avoid the degeneration of the antioxidants in djulis caused by high temperature of heating.

In the step of "condensation S3", the mixture is condensed to obtain a djulis paste. In the present embodiment, the djulis is but not limited to condense via a decompressed condensed method to obtain a concentrate. As following, the concentrate is dilute in distilled water till at a concentration of 0.2 g/ml to obtain the djulis paste of the present invention.

Additionally, a process of "grinding S4," can be also performed either after the step of "mixing S1" or the step of "heating S2". In the process of "grinding S4," the djulis powder of the present invention can be ground in the form of a nanoparticle, for example 20 to 70 nm, so that the cell wall of the djulis will be destroyed, and the antioxidants of the djulis can be easily released. In the present embodiment the nanoparticle of the djulis powder is but not limited to obtain by a nano wet grinding machine.

Furthermore, a process of "enzyme degradation S5," can be further performed either after the step of "mixing S1," the step of "heating S2," or the step of "condensation S3". In the process of "enzyme degradation S5," an amylase is co-incubate with the djulis powder, the mixture or the djulis paste of the present invention at 37° C. for 4 to 8 hours for enzymatic processing, in order to obtain an enzymatic solution. In the present embodiment, the processed time of the amylase is 6 hours. With the arrangement of the process of "enzyme degradation S5," the starch in the djulis can be enzymatically degraded into glucose and maltose, and which will be much easier in use and manufacture.

For proving the effects of the djulis of the present invention, various samples of djulis and oats are prepared for undergoing a serial test in anti-oxidant activity. With reference to TABLE 1, the samples of djulis are divided into 4 groups including (a) under process of the step of "mixing S1" only; (b) under process of the steps of "mixing S1," "heating S2," and "condensation S3"; (c) under process of the steps of "mixing S1," "heating S2," and "condensation S3," and the processes of "grinding S4," and "enzymatic degradation S5"; and (d) under process of the step of "mixing S1," and a process of artificial gastric juice, and the samples of oats are divided into 2 groups including (e) under process of the step of "mixing S1" and the process of artificial gastric juice and (f) under process of the step of "mixing S1," and "enzymatic degradation S5". In the present embodiment, the process of artificial gastric juice is carried out by adjusting the pH value of the samples of djulis or oats to 1.2, and co-incubating the samples of djulis or oats with pepsin (3.2 mg/100 ml) for 2 hours. The process of artificial gastric juice can predict the normal digestion of oats and djulis in organisms.

TABLE 1

Samples Arrangement of Oats and Djulis

| Groups | Particles | Process |
| --- | --- | --- |
| a | microparticle | S1 only |
| b | microparticle | S1 + S2 + S3 |
| c | nanoparticle | S1 + S2 + S3 + S4 + S5 |
| d | microparticle | S1 + artificial gastric juice |
| e | microparticle | S1 + artificial gastric juice |
| f | microparticle | S1 + S5 |

Referring to TABLE 2, the concentration of antioxidants, such as polyphenols, SOD and betalains in the five groups of oats and djulis is detected and listed. Also, the scavenging of 2,2-Diphenyl-1-picryl-hydrazyl (DPPH) and the fluorescence recovery after photobleaching (FRAP) in the six groups of oats and djulis is monitored and recorded in the TABLE 2.

In the present embodiment, 0.01 g/ml of the djulis or oats is used in the serial test in antioxidant activity.

TABLE 2

Concentration of Antioxidants in Oats and Djulis

| Groups | Betalains (μm) | SOD (U/mg protein) | Polyphenols (mg/100 ml) | DPPH-scavenging (%) | FRAP (μmole/L) |
|---|---|---|---|---|---|
| (a) | 13 | 2.59 | 35.01 | 1140.8 | 24.05 |
| (b) | 13 | 2.26 | 35.97 | 1204.8 | 24.63 |
| (c) | 13 | 5.82 | 43.16 | 1161.8 | 39.15 |
| (d) | 11 | 4.97 | 64.55 | 2003.8 | 58.02 |
| (e) | — | 6.18 | 26.63 | 144.8 | 40.16 |
| (f) | — | 9.26 | 10.57 | 71.8 | 10.12 |

According to TABLE 2, in compare to groups (a) and (b), a higher level of SOD, polyphenols and betalains, and better activity in DPPH-scavenging and FRAP can be observed in the group (c). It is believed that, djulis with nanoparticle shows better antioxidant activity than djulis with microparticle. Moreover, the results of the group (d) suggest that the antioxidant activity, DPPH-scavenging and the FRAP of the djulis of the present invention are quite effective even after the digestion of organisms. It is noted that the active substances, also the antioxidant activity of the djulis will not be inactivated under an acid condition in digestive system of organisms.

In additional, compare with the oats in groups (e) and (f), the djulis has better activity in DPPH-scavenging and FRAP due to its extra content of betalains and higher content of polyphenols. It is suggested that the djulis of the present invention shows notable ability in DPPH-scavenging and FRAP, and therefore the djulis will be more effective against to hyperlipidemia or hypercholesterolemia than oats do.

In order to further prove the therapeutic effects of the djulis in hyperlipidemia or hypercholesterolemia, an animal trial is carried out by preparing an experimental animal with hyperlipidemia-related syndrome and examining levels of total cholesterol (TC), triglyceride (TG), low-density lipoprotein-cholesterol (LDL-C), and high-density lipoprotein-cholesterol (HDL-C) of the experimental animal. In the present embodiment, a commercial kit-enzyme-colorimetric kit HUMAN GmbH (Wiesbaden, Germany) is used to analyze the levels of TC, TG, LDL-C and HDL-C in the experimental animal.

In the present embodiment, the experimental animal is male, four weeks old specific-pathogen-free hamster, and which is collected from National Laboratory Animal Center in Taiwan, and maintained in a temperature-controlled facility ($25\pm1°$ C.) with a 12-hours light/dark cycle. Before the animal trial, the hamsters are fed high-fat diet for four weeks, in order to obtain experimental hamsters of the present invention with hyperlipidemia and hypercholesterolemia. In the present embodiment the high-fat diet contains 10% of fat and 2% of cholesterol. Also, weight of each experimental hamster is monitored every week during the period of feeding high fat diet and during the trial.

Figure 2:
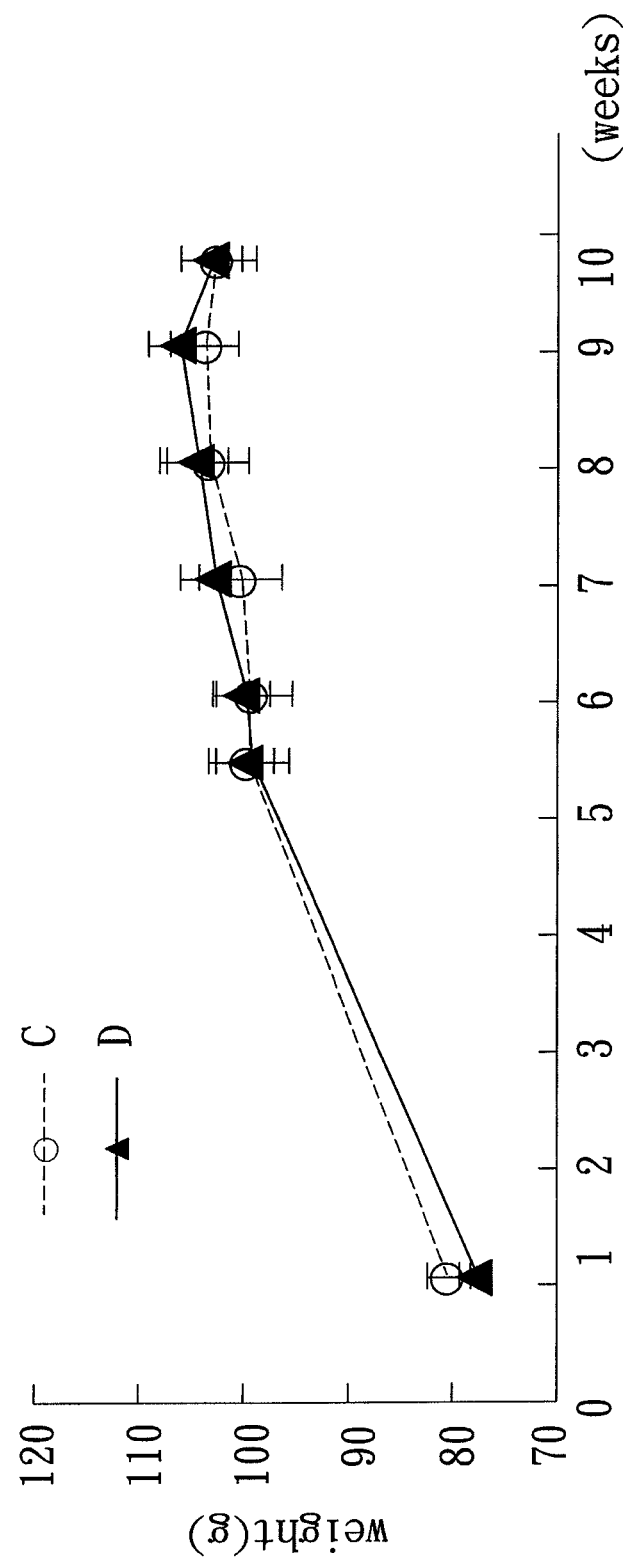
FIG. 2 is a line chart illustrating the change of weight of experimental hamsters.
Figure 3:
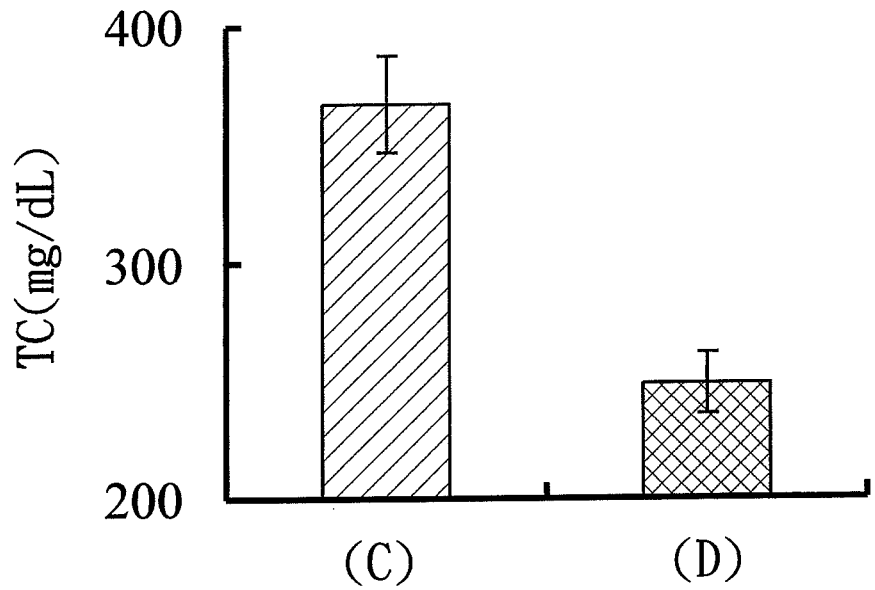
FIG. 3 is a bar chart illustrating the level of total cholesterol (TC) in experimental hamsters
Figure 4:
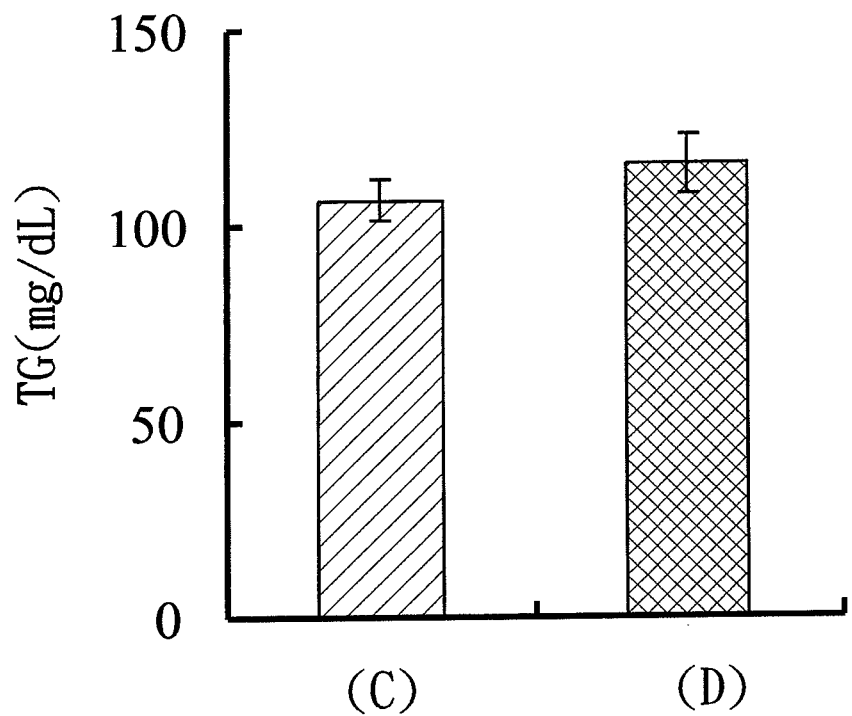
FIG. 4 is a bar chart illustrating the level of triglyceride (TG) in experimental hamsters.
Figure 5:
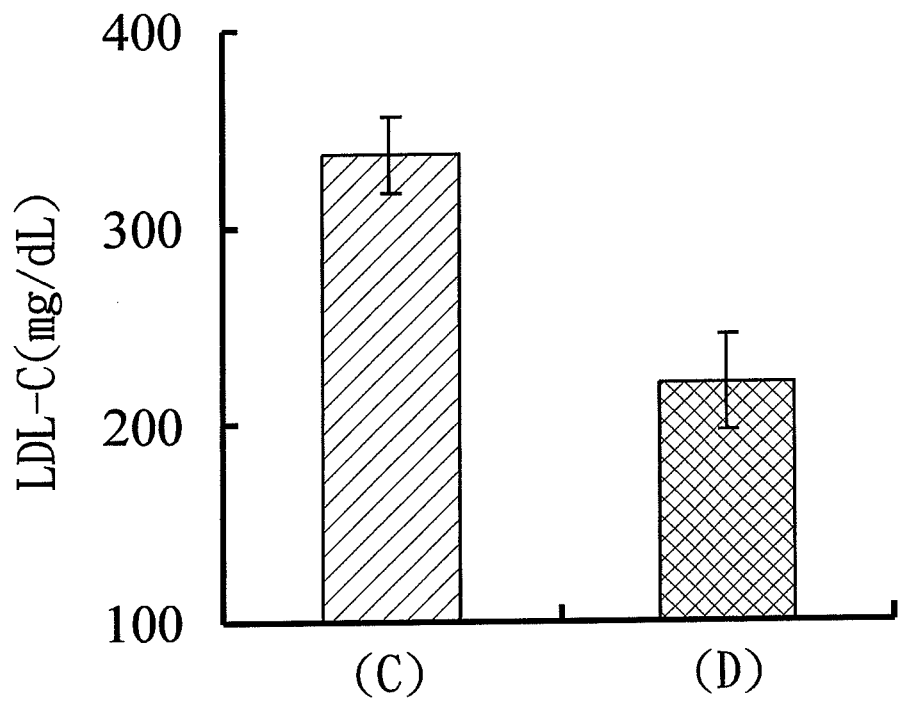
FIG. 5 is a bar chart illustrating the level of low-density lipoprotein-cholesterol (LDL-C) in experimental hamsters.
Figure 6:
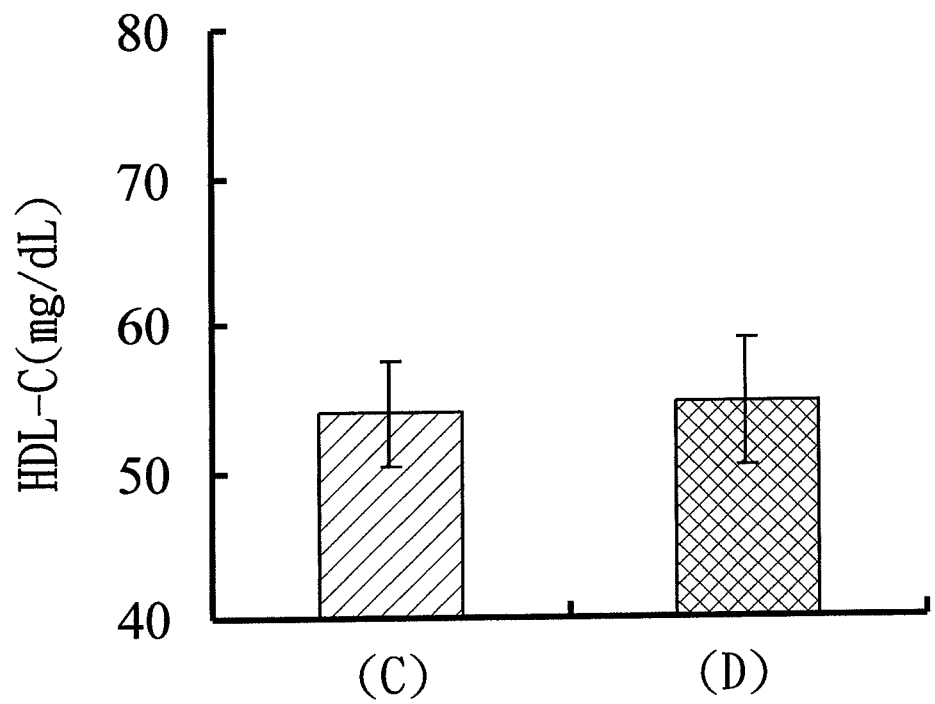
FIG. 6 is a bar chart illustrating the level of high-density lipoprotein-cholesterol (HDL-C) in experimental hamsters.
Figure 7:
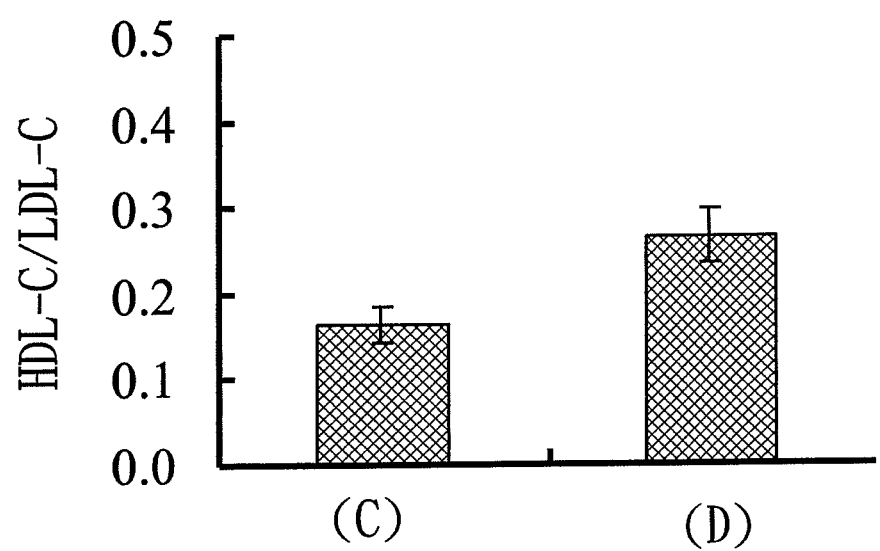
FIG. 7 is a bar chart illustrating the ratio of the high-density lipoprotein-cholesterol (HDL-C) to the low-density lipoprotein-cholesterol (LDL-C) in experimental hamsters.

Referring to FIG. 2, the experimental hamsters are randomly divided into two groups comprising (C) a control group and (D) a djulis group, wherein the experimental hamsters in the control group (C) only fed 0.85% of saline during the trial, but the experimental hamsters in the djulis group (D) fed the djulis paste of the present invention during the trial. In the present embodiment weight of experimental hamsters in each group are monitored and summarized in FIG. 2. It is showed that the experimental hamsters whatever in groups (C) or (D) all gain some weight after having a high-fat diet, with around 20 to 25 grams of weight gained in average. In the present embodiment, the djulis paste of the present invention is obtain by processing steps of "mixing S1," "heating S2," and "condensation S3," and processes of "grinding S4," and "enzymatic degradation S5," and which is rich in dietary fiber, protein and starch. The detail contents of the djulis of the present invention are summarized in TABLE 3. Generally, the concentration of the djulis paste of the present invention is 0.2 g/ml and a preferable dosage of the djulis paste is approximately at 0.2 to 1.0 g for per kilogram of experimental hamster. In the present embodiment, the dosage of the djulis of the present invention is 1.0 g/per kilogram of hamster.

TABLE 3

Contents of the Djulis

| Items | Contents |
|---|---|
| Dietary fiber (%) | 16.3 |
| Protein (%) | 17.5 |
| Starch (%) | 40.8 |
| Polyphenols (mg/100 ml) | 41.39 |
| Betalains (μM) | 14 |
| SOD (U/mg protein) | 9.55 |
| DPPH-scavenging (%) | 47.05 |
| FRAP (μmole/L) | 1142.8 |

In TABLE 4 and FIGS. 3 to 7, the value of the total cholesterol and the low-density lipoprotein-cholesterol in the djilus group (D) is significantly lower than that in the control group (C). It is noted that the djulis of the present invention can dramatically reduce the level of the total cholesterol, as well as the low-density lipoprotein-cholesterol in organisms, especially in organisms with hyperlipidemia. It is proved that, the djulis of the present invention is sufficient to control the incidence of the cardio-cerebrovascular diseases. In this way, the high mortality of the cardio-cerebrovascular diseases can be improved.

TABLE 4 cholesterol level in experimental hamsters

| | (C) | (D) |
|---|---|---|
| TC (mg/dL) | 367 | 250 |
| TG (mg/dL) | 110 | 115 |
| LDL (mg/dL) | 335 | 225 |
| HDL (mg/dL) | 54.3 | 55.7 |
| HDL/LDL | 0.17 | 0.27 |

In summary, the active substance comprised djulis is provided in the present invention, and which is potential to be developed and applied to medication or health product for hyperlipidemia and hypercholesterolemia. Preferably, the djulis is used at a dosage of 0.2 g to 1.0 g for per kilogram of organisms and it can be manufactured into any form of medication or health product, for example, pill, capsule, powder, solution and pastil. Generally, the active substance of the present invention can be given to patients individually or combined with other acceptable medicaments, excipient, acceptable carriers or nutrients, for efficiently preventing from hyperlipidemia, hypercholesterolemia or cardio-cerebrovascular diseases.

Through the present invention, the active substance of health product or medication for hyperlipidemia and hypercholesterolemia is provided and comprises. The djulis of the present invention is processed by steps of "mixing S1," "heating S2," "condensation S3," "grinding S4," and "enzymatic degradation S5," which makes the djulis of the present invention easy to be absorbed and biodegraded. Furthermore, the djulis of the present invention is rich in dietary fiber, polyphenols, betalains and SOD so that it can dramatically inhibit the absorption of cholesterol in cells, advance the metabolism of cholesterol, and also improve the antioxidant activity of organisms. With such benefits of the djulis of the present invention, it is sufficient to avoid the accumulation of oxidized low-density lipoprotein-cholesterol (oxLDL-C) in vessel walls and to control the incidence of hyperlipidemia, hypercholesterolemia, and cardio-cerebrovascular diseases. It is believed that the djulis of the present invention has better therapeutic effects in hyperlipidemia and hypercholesterolemia than other conventional natural substance for hyperlipidemia and hypercholesterolemia, for example *Hibiscus sabdariffa* and *Avena sativa*.

Although the invention has been described in detail with reference to its presently preferred embodiment, it will be understood by one of ordinary skill in the art that various modifications can be made without departing from the spirit and the scope of the invention, as set forth in the appended claims.

What is claimed is:

1. A composition for treating hyperlipidemia and hypercholesterolemia comprising a therapeutically effective amount of djulis paste, wherein the diulis paste is manufactured by preparing a sample of *Chenopodium formosanum* Koidz., grinding the sample of *Chenopodium formosanum* Koidz, into a plurality of microparticles of 1 to 20 micrometers (μm) in size, mixing the plurality of microparticles with distilled water to obtain a microlized mixture, grinding the microlized mixture into a nanolized mixture comprising a plurality of particles of 20 to 70 nanometers (nm) in size, heating the nanolized mixture at 65 to 85° C. for 0.5 to 1 hour, processing the nanolized mixture with an amylase at 37° C. for 4 to 8 hours to obtain an enzymatic solution, and condensing the enzymatic solution to obtain the djulis paste, wherein the therapeutically effective amount of djulis paste is an amount effective for treating hyperlipidemia and hypercholesterolemia.

2. The composition for treating hyperlipidemia and hypercholesterolemia as defined in claim 1, wherein the composition is in the form of a pastille, pill, capsule, powder or solution.

3. A method of treating hyperlipidemia and hypercholesterolemia comprising administering a therapeutically effective dosage of the composition as defined in claim 1 to a mammal in need thereof.

4. The method of treating hyperlipidemia and hypercholesterolemia as defined in claim 3, wherein the therapeutically effective dosage is 200-1000 milligrams (mg) per kilogram (kg) of the body weight of the mammal.

* * * * *